(12) United States Patent
Frank et al.

(10) Patent No.: US 11,377,653 B2
(45) Date of Patent: Jul. 5, 2022

(54) METHOD FOR EXTRACTING DNA

(71) Applicant: Füll Process SA, Altnau (CH)

(72) Inventors: Joel Johannes Frank, Offenburg (DE); Thomas Brinz, Bissingen A.D. Teck (DE)

(73) Assignee: Füll Process SA, Altnau (CH)

( * ) Notice: Subject to any disclaimer, the term of this patent is extended or adjusted under 35 U.S.C. 154(b) by 25 days.

(21) Appl. No.: 16/476,590

(22) PCT Filed: Nov. 8, 2017

(86) PCT No.: PCT/EP2017/078538
§ 371 (c)(1),
(2) Date: Jul. 9, 2019

(87) PCT Pub. No.: WO2018/130319
PCT Pub. Date: Jul. 19, 2018

(65) Prior Publication Data
US 2019/0367906 A1    Dec. 5, 2019

(30) Foreign Application Priority Data

Jan. 11, 2017   (DE) ................ 10 2017 200 332.4

(51) Int. Cl.
*C12N 15/10*    (2006.01)
*B01L 3/02*    (2006.01)
(Continued)

(52) U.S. Cl.
CPC ........ *C12N 15/1017* (2013.01); *B01L 3/0206* (2013.01); *B01L 3/50255* (2013.01);
(Continued)

(58) Field of Classification Search
CPC .............. C12N 15/1017; B01L 3/0206; B01L 3/50255; B01L 3/56; B01L 2300/0829;
(Continued)

(56) References Cited

U.S. PATENT DOCUMENTS

2007/0184548 A1* 8/2007 Tan ..................... B01L 7/52
435/303.1
2014/0283945 A1* 9/2014 Jones ................ B01L 3/502
141/1
(Continued)

FOREIGN PATENT DOCUMENTS

DE         69524560        5/2002
DE        102013215575     2/2015
(Continued)

OTHER PUBLICATIONS

International Search Report for Application No. PCT/EP2017/078538 dated Jan. 5, 2018 (English Translation, 2 pages).

*Primary Examiner* — Jennifer Wecker
*Assistant Examiner* — Oyeleye Alexander Alabi
(74) *Attorney, Agent, or Firm* — Michael Best & Friedrich LLP

(57) ABSTRACT

The invention relates to a method for extracting DNA, comprising the steps of: providing (400) a lysate (11) in a sample vessel (1), feeding (500) an DNA absorbing substance (15) to the sample vessel (1), closing (700) the sample vessel (1) by means of a wash filter element (3), feeding (600) a wash fluid (12) to the sample vessel (1) through the wash filter element (3), and discharging (700) the wash fluid (12) from the sample vessel (1) through the wash filter element (3). The DNA absorbing substance can be retained from the wash filter element (3).

20 Claims, 17 Drawing Sheets

(51) Int. Cl.
  *B01L 3/00* (2006.01)
  *G01N 35/10* (2006.01)
  *G01N 35/00* (2006.01)

(52) U.S. Cl.
  CPC ............ *B01L 3/56* (2013.01); *G01N 35/1002* (2013.01); *G01N 35/1009* (2013.01); *B01L 2300/0829* (2013.01); *B01L 2400/049* (2013.01); *B01L 2400/0478* (2013.01); *G01N 2035/00475* (2013.01)

(58) Field of Classification Search
  CPC ....... B01L 2400/0478; B01L 2400/049; G01N 35/1002; G01N 35/1009; G01N 2035/00475
  See application file for complete search history.

(56) References Cited

U.S. PATENT DOCUMENTS

| | | | | |
|---|---|---|---|---|
| 2015/0368635 | A1* | 12/2015 | Lo | B01L 3/502715 204/601 |
| 2016/0017316 | A1* | 1/2016 | Saghbini | C12N 15/1017 435/270 |
| 2016/0083781 | A1* | 3/2016 | Cooney | C12Q 1/6806 435/6.12 |
| 2017/0029809 | A1* | 2/2017 | Suh | C12N 15/1003 |

FOREIGN PATENT DOCUMENTS

| | | | | |
|---|---|---|---|---|
| DE | 102013215575 A1 | * | 2/2015 | ............... C12N 1/06 |
| WO | 2015018647 | | 2/2015 | |

\* cited by examiner

METHOD FOR EXTRACTING DNA

BACKGROUND OF THE INVENTION

The present invention relates to a method for extracting DNA. In particular, the invention relates to a method for the automated extraction, particularly advantageously for the automated purification, of DNA. In the scope of this invention, DNA is intended to mean deoxyribonucleic acid.

Methods for extracting DNA are known from the prior art. To this end, DNA is separated from cellular material. Subsequently, so-called magnetic beads are used, which are small magnetic particles that form a bond with DNA. In this way, it is possible to purify DNA. The method is based on DNA reversibly binding to such particles, for example to silicon dioxide, in highly concentrated salt solutions.

First, the cells are broken up and a lysate is formed, which contains both the released DNA and residual substances of the cells. Chaotropic salts, which interfere with or entirely disrupt the regular structure of water and prevent hydrophobic interactions, are added to the mixture.

The described beads, which are coated with silicon dioxide or another strongly DNA-adsorbing substance, are added to the mixture. The DNA therefore forms a specific bond with the silicon dioxide on the surface of the beads. The magnetic property of the beads permits magnetic fixing of the DNA. At the same time, residual substances, such as, in particular, cellular debris, can be washed out from the mixture. In order to break the bonding of the DNA to the beads, in the final step washing is carried out with a solution that no longer contains chaotropic salts. Using a magnet, the beats can then be separated from the DNA, so that the DNA is available for further steps.

A method for the continuous extraction of DNA is also described, for example, in DE 10 2013 215 575 A1.

SUMMARY OF THE INVENTION

The method according to the invention permits fully automated extraction and/or purification of DNA without the intervention of a human. In particular, at the start cellular materials are provided in special sample vessels. A fully automatedly operating machine may subsequently carry out the extraction and/or purification of the DNA according to predetermined protocols and/or procedures. To this end, it is merely necessary to assign each sample a procedure, which is the only intervention by a human. In particular, the method is simplified by the fact that the DNA does not leave the sample vessel throughout the entire process.

The method for extracting DNA comprises the following steps:

first, a lysate is provided in a sample vessel. A lysate is, in particular, an emulsion in which the damaged cellular material is present. In particular, an outer cell membrane of the cells of the cell material is damaged or disrupted. Subsequently, a DNA-adsorbing substance is added to the sample vessel. DNA-adsorbing substances are known. Advantageously, the DNA-adsorbing substance is a substance that can be retained by a wash filter element. In a subsequent step, the wash filter element is applied to the sample vessel. Subsequently, a wash fluid is delivered through the wash filter element into the sample vessel, and the wash fluid is then discharged from the sample vessel through the wash filter element. The effect achieved in this way is that the wash filter element retains DNA because of the DNA-adsorbing substance, but at the same time is permeable for substances that are intended to be washed out. Such substances are, in particular, cellular waste, i.e. residues of the cell material, as well as other components which are not adsorbed by the DNA-adsorbing substance. The DNA remains in the sample vessel since it is retained by the wash filter element because of the DNA-adsorbing substance. The delivery and discharge of the wash fluid can be automated in a simplified way, in particular optimally, by the method. In particular, the simplification results from the fact that the DNA does not leave the sample vessel throughout the entire process. Rather, wash fluid is delivered and discharged constantly. The delivery and discharge take place through the wash filter element, so that there only needs to be a single connection between the outer environment and the sample vessel. Said connection is produced through the wash filter element.

The method according to the invention for extracting DNA advantageously comprises release of the DNA from a cellular material and a washing process for purifying the DNA. The release from the cellular material is carried out by means of the above-described step of providing the lysate. The washing process is carried out by the other steps described above. In this way, DNA can be extracted reliably, the entire process required therefor being automatable and therefore taking place rapidly and economically. In the method according to the invention, all the process steps are preferably carried out serially.

The dependent claims contain preferred refinements of the invention.

Preferably, it is provided that the step of providing the lysate comprises the following steps: first, cellular material is introduced into an additional sample vessel. Furthermore, a grinding element is introduced into the additional sample vessel. The grinding element is, in particular, a grinding ball. Subsequently, the cell material is broken down by moving the additional sample vessel. To this end, the additional sample vessel is advantageously closed. The movement is carried out, in particular, by high-frequency alternating movement of the additional sample vessel. In one particularly advantageous configuration, the additional sample vessel is configured cylindrically, a movement taking place in particular along a midaxis of the cylindrical shape. In this way, the grinding ball is used to break down the cells of the cellular material. Lastly, a step of filtering the lysate out from the additional sample vessel into the above-described sample vessel through a lysate filter element is carried out. A single change between the additional sample vessel and the sample vessel therefore preferably takes place throughout the entire method, the filtered-out lysate no longer leaving the sample vessel throughout the entire method. In particular, this ensures that cellular material that has not been broken down, as well as coarse cellular waste, which is significantly larger than the DNA, remains in the additional sample vessel. The lysate provided in the sample vessel therefore merely needs to be purified by means of the above-described purification by delivering and discharging a wash fluid. The DNA is subsequently available for further steps. The above-described steps of introducing cellular material into the additional sample vessel, the introduction of the grinding element, the breaking down of the cellular material and the filtering out of the lysate can also be carried out simply and with little outlay. Said steps can therefore be automated simply and with little outlay in order to rapidly and reliably permit provision of lysate in the sample vessel. Again, provision is preferably made that no interventions whatsoever of a human are required.

Advantageously, provision is made that the wash filter element or the lysate filter element is arranged in a plunger.

In this case, provision is made that the plunger is insertable into the sample vessel or the additional sample vessel. Furthermore, provision is made that the plunger allows delivery and/or discharge of wash fluid. This is achieved in that, through the plunger, the wash fluid is sucked into the sample vessel and pressed out from the sample vessel. The plunger therefore has an opening which allows suction and pressing out of wash fluid. The wash filter element is furthermore located in the opening, so that the above-described delivery and discharge of wash fluid is possible only through the wash filter element. As an alternative, the plunger is configured in such a way that the lysate is pressed through the plunger from the additional sample vessel into the sample vessel. Again, the plunger preferably has an opening through which the lysate can be pressed. The lysate filter element is located inside the opening, which ensures that only the filtered-out lysate is transferred into the sample vessel. The formation of the plunger therefore simplifies said steps. The plunger is, in particular, configured in such a way that it has a cylindrical shape. The sample vessel and the additional sample vessel advantageously likewise have a cylindrical shape, the plunger being insertable into the sample vessel or the additional sample vessel. Particularly advantageously, a fluid-tight seal is formed on an outer circumferential surface of the plunger and on an inner circumferential surface of the sample vessel or of the additional sample vessel, so that fluid exchange can take place between the sample vessel and the environment only through the opening of the plunger.

The plunger and the sample vessel or the additional sample vessel particularly advantageously form a syringe. Suction of external fluids into the sample vessel is therefore made possible by relative movement of the plunger and the sample vessel or additional sample vessel with respect to one another, and at the same time by such a relative movement the content of the sample vessel can be pressed out. Fluid can therefore be introduced into the sample vessel and extracted from the sample vessel simply and with little outlay. Furthermore, the formation of the syringe allows accurate dosing of the fluid to be taken in or taken out. Lastly, the delivery and discharge of fluid to or from the sample vessel or the additional sample vessel is simply automatable, so that human intervention is not necessary. Since the delivery and discharge of wash fluid take place only through the wash filter element, the syringe, in particular the plunger, is constructed very simply since it is only necessary to provide a single opening through which the delivery and discharge of the wash fluid take place.

Throughout the entire method, in particular during the washing process, the sample vessel is advantageously held in a holding device. As an alternative or in addition, the additional sample vessel is held in an additional holding element at least during the provision of the lysate. The sample vessel can preferably be fixed in the holding element. Likewise, the additional sample vessel can preferably be fixed in the additional holding element. By movement of the holding element and/or of the additional holding element, movement of the sample vessel or of the additional sample vessel can therefore be achieved. Since there is advantageously fluid-tightness because of the use of the above-described plunger, turning or tilting of the sample vessel or of the additional sample vessel may therefore also take place. In this case, it is ensured that the sample vessel is held securely and reliably in the holding device, while the additional sample vessel is held securely and reliably in the additional holding device.

Particularly advantageously, a multiplicity of sample vessels are held simultaneously in the holding element. It is likewise particularly advantageous for a multiplicity of additional sample vessels to be held in the additional holding element. The above-described method steps are therefore preferably carried out simultaneously on a multiplicity of sample vessels or additional sample vessels. A multiplicity is, in particular, intended to mean an even number of sample vessels or additional sample vessels. Particularly advantageously, a multiplicity is intended to mean a number of at least four. All the sample vessels are therefore held by a single holding element, all the sample vessels being fixable in the holding element. Fixing or detachment of the sample vessels in the holding element is advantageously carried out simultaneously. This also applies similarly for the additional sample vessels, so that the multiplicity of additional sample vessels are held in a single additional holding element. In this case as well, the fixing or release of the additional sample vessels can be carried out simultaneously. In particular, this makes it possible for a large multiplicity of individual sample vessels or additional sample vessels to be able to be handled simultaneously. The method can therefore advantageously be automated, so that a high throughput can be achieved in a minimized time.

According to another particularly preferred embodiment, a multiplicity of plungers are fixed on a carrier element. The multiplicity of plungers are advantageously identical to the multiplicity of sample vessels and/or additional sample vessels. The multiplicity of plungers can therefore be inserted simultaneously into the multiplicity of sample vessels and/or additional sample vessels. This in turn improves the automatability, so that a multiplicity of sample vessels and/or additional sample vessels can be processed simultaneously. The plungers are, in particular, connected to the carrier element with a form fit.

Particularly advantageously, the delivery of wash fluid and/or the discharge of wash fluid and/or the filtering out of the lysate are carried out by moving the carrier element and the holding element or the additional holding element relative to one another. Particularly advantageously, the holding element is moved relative to the carrier element. This makes simplified delivery or discharge of wash fluid possible, as well as simplified filtering out of the lysate. In particular, simplified automatability is therefore achieved, it being possible to simultaneously process a large multiplicity of sample vessels and/or additional sample vessels.

According to another advantageous embodiment, the delivery of wash fluid is carried out by simultaneous suction of wash fluid through the multiplicity of plungers from a common reservoir. As an alternative, the suction through the multiplicity of plungers is carried out from respective individual reservoirs, an individual reservoir being assigned to each plunger. The delivery of wash fluid is advantageously carried out in such a way that the opening of the plunger is brought in contact with the wash fluid, in particular immersed in the wash fluid. Movement of the holding element is subsequently carried out, the holding element being removed from the carrier element and the reservoir or the multiplicity of individual reservoirs. In this way, a reduced pressure is generated inside the sample vessels, so that the wash fluid is sucked through the plunger. In order to discharge the wash fluid, and oppositely directed movement of the holding element is carried out, so that the wash fluid is pressed out from the sample vessels. Particularly advantageously, discharge of the wash fluid is carried out into a separate waste container.

Advantageously, provision is made that the reservoir is subdivided by at least one subdivision element into individual subreservoirs for each plunger. The at least one subdivision element is advantageously retractable, and therefore removable from the reservoir. The reservoir can therefore be filled simply with the wash fluid, subreservoirs subsequently being delimited by the subdivision element so that a separate subreservoir is available for each plunger.

The above-described steps of delivering wash fluid and discharging wash fluid are advantageously carried out repeatedly. The repetition of the steps is particularly advantageously carried out with different wash fluid. Secure and reliable cleaning of the DNA therefore takes place. In particular, by the repeated delivery and discharge of, in particular, different wash fluids, the DNA can be purified comprehensively. The method therefore allows secure and reliable provision of pure DNA. For the repeated delivery and discharge of wash fluid, it is in particular possible always to use the same plunger. The plunger may be rinsed and/or cleaned before reuse for the delivery and discharge of wash fluid. As an alternative, a new plunger may also be used for each new conduct of the steps of delivering and discharging wash fluid. Since the steps of delivering and discharging wash fluid by the above-described use of the plunger can be automated simply and with little outlay, an arbitrary number of repetitions may be carried out without significantly increasing the overall process time for the extraction of DNA. It likewise prevents an outlay for carrying out the method, that is to say an outlay for carrying out the extraction of the DNA, from becoming uneconomically high.

Particularly advantageously, after the delivery of the wash fluid and before the discharge of the wash fluid, loosening of the filter cake which is located on the wash filter element is carried out. To this end, air is delivered to the sample vessel. The delivery of air is, in particular, carried out in the same way as the delivery of the wash fluid. The filter cake can therefore be mixed optimally with the wash fluid.

The delivery of the wash fluid and the discharge of the wash fluid is used, in particular, for purifying the DNA. Therefore, provision is particularly advantageously made that, after the delivery of the wash fluid and before the discharge of the wash fluid, the sample vessel is moved, particularly with a high frequency, circularly or alternatingly. In this way, a filter cake that is present on the wash filter element is released and/or loosened.

This achieves the effect that the filter cake is mixed optimally with the wash fluid. Since the filter cake is formed by the DNA, optimal washing of the DNA therefore takes place.

According to one particularly advantageous embodiment, the wash filter element and the lysate filter element are identical. This means that only a single type of filter element needs to be provided in order to carry out the entire method as described above. This means that only one type of plunger needs to be provided. The wash filter element and the lysate filter element are advantageously used for retaining DNA only when they are provided with a DNA-adsorbing substance. The DNA can therefore be extracted simply and with little outlay, since the same filter element can always be used for different method steps.

After the delivery of the wash fluid, an additional substance is preferably introduced into the sample vessel. To this end, an additional substance which releases the DNA-adsorbing substance from the DNA is, in particular, added to the sample vessel. This means that the DNA is available for further steps after the addition of the additional substance. The DNA is thereby highly purified by the method previously carried out. Additional substances for releasing the DNA-adsorbing substance from the DNA are known from the prior art.

BRIEF DESCRIPTION OF THE DRAWINGS

Exemplary embodiments of the invention will be described in detail below with reference to the appended drawings. In the drawings.

DETAILED DESCRIPTION

Figure 1:
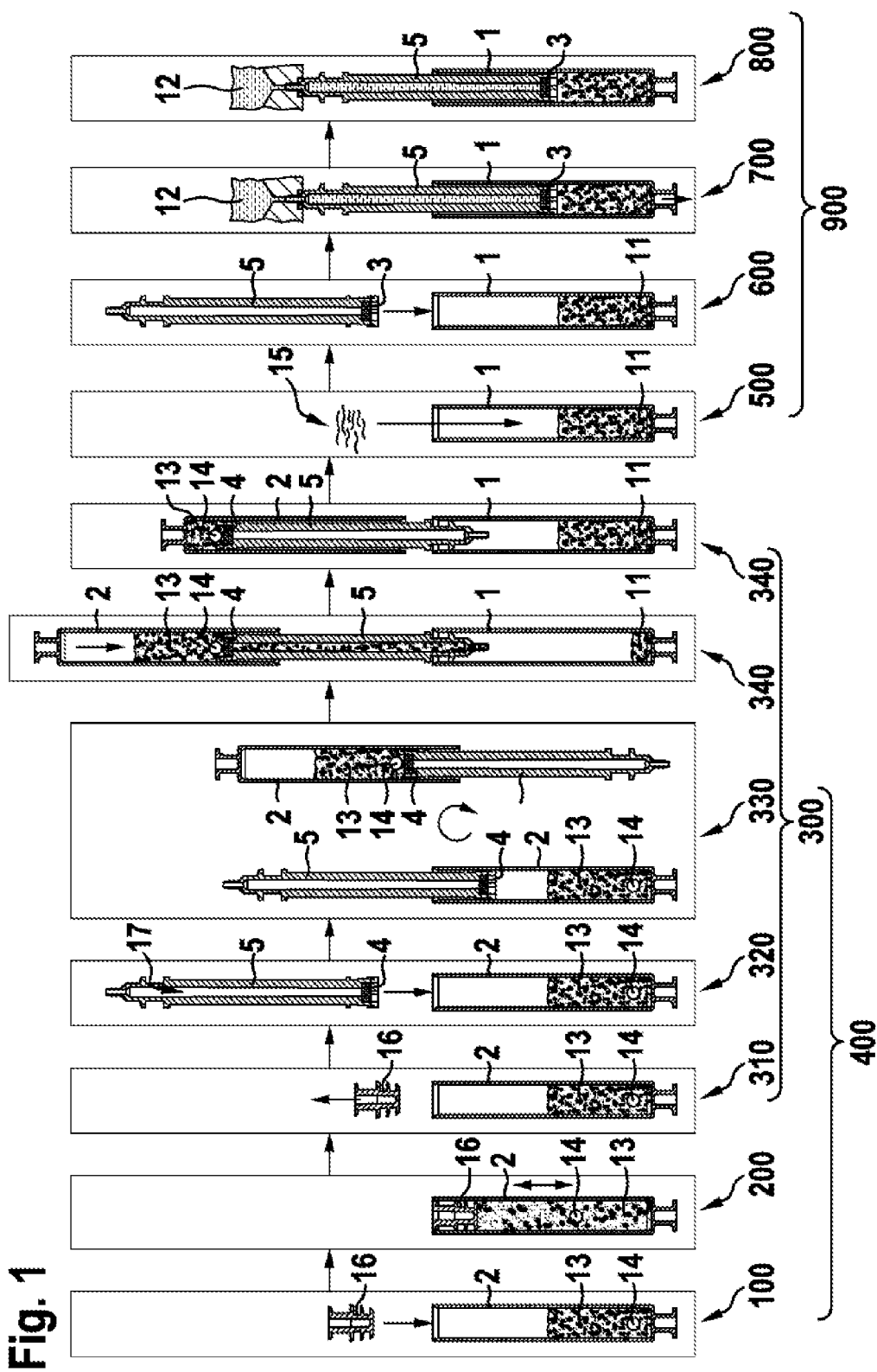
FIG. 1 shows a schematic view of a sequence of a method according to an exemplary embodiment of the invention.

FIG. 1 schematically shows a sequence of a method according to an exemplary embodiment of the invention.

The method is subdivided in particular into two steps, a step of providing 400 lysate 11 in a sample vessel 1, and a washing process 900 in order to purify the DNA inside the lysate 11.

The step of providing 400 the lysate 11 comprises, in particular, a plurality of substeps. Thus, introduction 100 of cellular material 13 and of a grinding element 14 into an additional sample vessel 2 is initially carried out. The grinding element 14 is, in particular, a grinding ball. Subsequently, closure of the additional sample vessel 2 is carried out by means of a stopper 16.

After the introduction step 100, breakdown 200 of the cellular material 13 is carried out. To this end, the additional sample vessel 2 is moved alternatingly, in particular alternatingly with a high frequency. Particularly advantageously, the additional sample vessel 2 is configured cylindrically, the alternating movement of the additional sample vessel 2 being carried out parallel to a midaxis of the cylindrical shape. The effect achieved by such a movement of the additional sample vessel 2 is that cells inside the cellular material 13 are broken down by the grinding element 14, so that the DNA can emerge from the cells.

After the breakdown step 200 has been carried out, the cellular material 13 is a mixture of cells not broken down, cells broken down and cell contents, which are located inside the additional sample vessel 2. In a further step, filtering 300 of the lysate 11 out into a sample vessel 1 is therefore carried out. For the filtering out 300, removal 310 of the stopper 16 is carried out. Instead of the stopper 16, a plunger 5 is used, so that after the removal 310, application 320 of the plunger 5 is carried out. The plunger 5, and preferably likewise the additional sample vessel 2, is configured cylindrically. The plunger 5 can therefore advantageously be introduced into the additional sample vessel 2. In this case, a fluid-tight seal is formed between an outer wall of the plunger 5 and an inner wall of the additional sample vessel 2.

The plunger 5 preferably comprises an opening 17. The opening 17 therefore constitutes a connection of the interior of the additional sample vessel 2 to an environment. The opening constitutes, in particular, a channel extending lengthwise along a midaxis of the cylindrical shape of the plunger 5, so that the plunger 5 has the shape of a hollow cylinder. A lysate filter element 4 is arranged in the opening 17, so that all fluid which is intended to pass through the plunger 5 into the additional sample vessel 2, or is intended to be removed from the additional sample vessel 2, must pass through the opening 17 and the lysate filter element 4.

The combination of the additional sample vessel 2 and the plunger 5 forms, in particular, a syringe. By relative movement of the additional sample vessel 2 and the plunger 5 with respect to one another, it therefore becomes possible to suck fluid into the additional sample vessel 2 or press it out from the additional sample vessel 2. This simplifies the delivery and discharge of fluid into or out from the additional sample vessel 2.

After the application 320 of the plunger 5, the additional sample vessel 2 is closed in a fluid-tight fashion, so long as no relative movement occurs between the plunger 5 and the additional sample vessel 2. Rotation 330 of the combination of the additional sample vessel 2 and the plunger 5 therefore takes place without the risk arising that the content of the additional sample vessel 2 will flow out. Lastly, pressing 340 of the lysate 11 out from the additional sample vessel 2 into the sample vessel 1 takes place. The pressing out 340 is initiated by the plunger 5 and the additional sample vessel 2 being moved relative to one another. Because of the lysate filter element 4, only the lysate 11 passes out of the additional sample vessel 2 through the plunger 5 into the sample vessel 1. The rest of the cellular material 13, i.e. in particular still intact cells as well as coarse cellular waste, are, just like the grinding element 14, retained by the lysate filter element 4. All undesired components therefore remain inside the additional sample vessel 2, while only the lysate 11 enters the sample vessel 1.

After the provision 400 of the lysate 11, the process 900 of washing the lysate 11 is carried out. The washing process 900 in turn comprises a multiplicity of substeps. In this case, provision is made that, at the start of the washing process 900, the lysate 11 is provided in a fresh sample vessel 1, the DNA contained in the lysate 11 no longer leaving the sample vessel 1 until the washing process 900 has ended.

First, supply 500 of a DNA-adsorbing substance 15 into the sample vessel 1 takes place. The DNA-adsorbing substance 15 is, in particular, silicon dioxide. The DNA-adsorbing substance 15 is, in particular, in a suspension. In this way, the dosing of the DNA-adsorbing substance 15 is simplified. Subsequently, closure 600 of the sample vessel 1 is carried out by means of a plunger 5, which comprises a wash filter element 3. The plunger 5 is, in particular, constructed identically to the plunger 5 previously used. Particularly advantageously, provision is furthermore made that the wash filter element 3 is identical to the wash filter element 4. Therefore, only a single type of plunger 5 is used for the entire method, that is to say in particular for the provision 400 and for the washing process 900. With the combination of the plunger 5 and the sample vessel 1, the sample vessel 1 is closed in a fluid-tight fashion. Introduction and discharge of fluid is possible only by moving the plunger 5 and the sample vessel 1 relative to one another, the fluid being conveyed through the plunger 5 and through the wash filter element 3.

After these preparation measures, in particular repeated delivery 700 of a wash fluid 12 and discharge 800 of the wash fluid 12 take place. In particular, a delivery 700 of different wash fluids 12 takes place, each wash fluid 12 being delivered only when the previous wash fluid 12 has been removed fully from the sample vessel 1 by the discharge step 800. Use of the different wash fluids 12 ensures that all the remaining cellular waste is removed from the lysate 11, in order to obtain DNA which is as pure as possible. During each discharge 800 of wash fluid 12, because of the DNA-adsorbing material 15 the DNA is retained by the wash filter element 12 and therefore remains inside the sample vessel 1 throughout the entire method.

In order finally to provide only DNA, reception of an additional substance into the sample vessel 1 is carried out. The additional substance is used to release the DNA-adsorbing substance 15 from the DNA. Maximally pure DNA is therefore available inside the sample vessel 1.

The method described above is, in particular, carried out in an automated fashion, a multiplicity of additional sample vessels 2 and/or sample vessels 1 being processed at the same time. To this end, a holding element 6 (cf. FIG. 2) is used, which can receive a multiplicity of sample vessels 1. Likewise, an additional holding element (not shown) preferably configured identically to the holding element 6 is used, which can receive a multiplicity of additional sample vessels 2. In this way, a multiplicity of sample vessels 1 and/or additional sample vessels 2 can be handled.

Furthermore, a carrier element 7 (cf. FIG. 2) is used in order to hold a multiplicity of plungers 5. In this way, a multiplicity of plungers 5 can be inserted simultaneously into a multiplicity of additional sample vessels 2, so as to simultaneously filter lysate 11 out from a multiplicity of additional sample vessels 2 into a multiplicity of sample vessels 1. The carrier element 7 may likewise be used in order to simultaneously insert a multiplicity of plungers 5 into the multiplicity of sample vessels 1. The effect achieved in this way is that the washing process 900 can be carried out simultaneously for the multiplicity of sample vessels 1. This is shown below in FIGS. 2 to 15.

Figure 2:
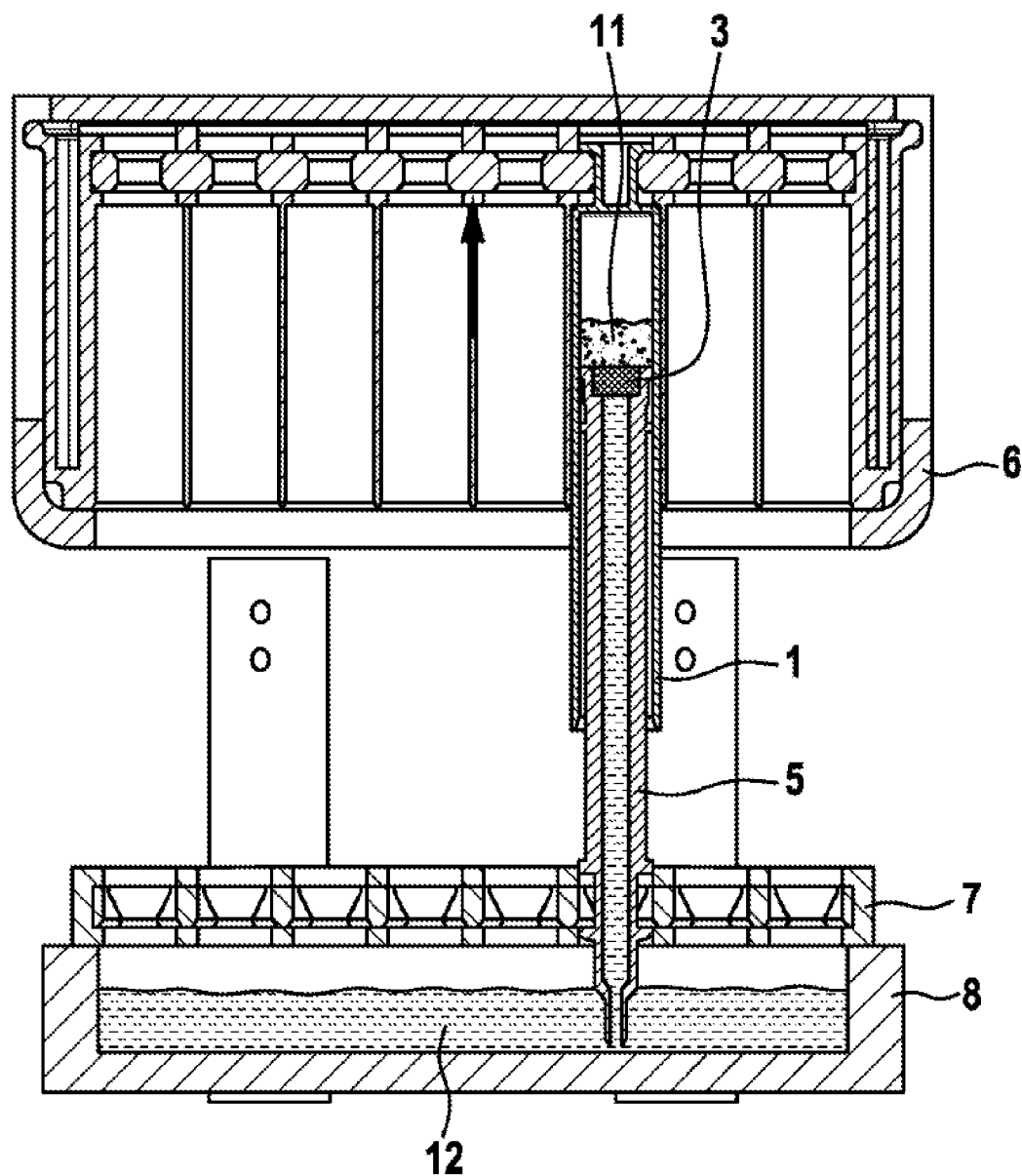
FIG. 2 shows a schematic view of a first alternative of a washing process of the method according to the exemplary embodiment of the invention.
Figure 3:
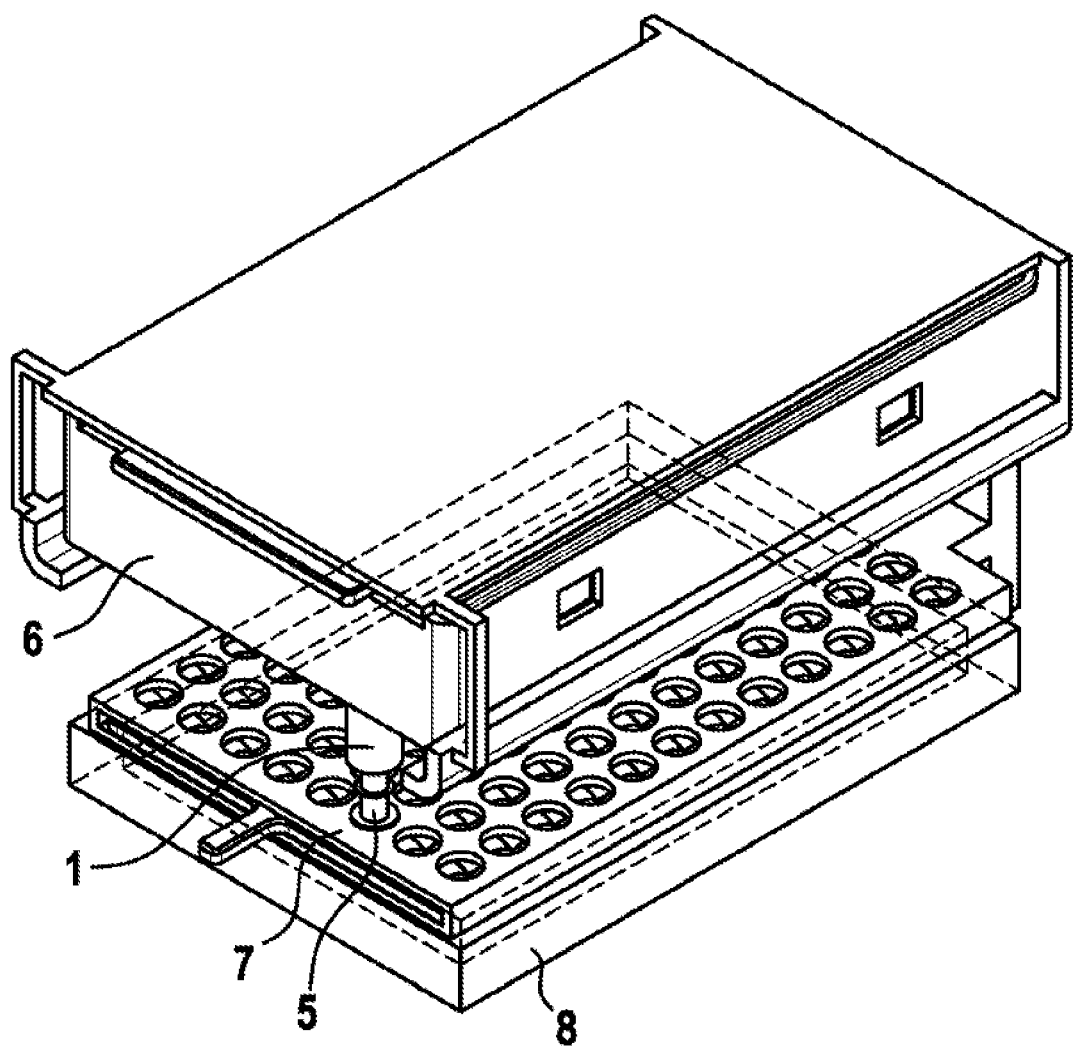
FIG. 3 shows a schematic view of the components used for carrying out the washing process according to the first alternative.

FIGS. 2 and 3 show a first alternative of the washing process 900. In the first alternative, suction of wash fluid 12 out from a common reservoir 8 takes place. The multiplicity of plungers 5 are immersed into the common reservoir 8. To this end, in particular, the carrier element 7 is placed onto the reservoir 8. Subsequently, a relative movement is carried out between the holding element 6 and the carrier element 7, during which the holding element 6 is moved away from the carrier element 7. In this way, a reduced pressure is generated inside the sample vessels 1, so that the wash fluid 12 is sucked through the plungers 5 into the sample vessels 1. There, the wash fluid 12 is mixed with the lysate 11 and subsequently pressed out from the sample vessel 1 by a new relative movement between the holding element 6 and the carrier element 7. To this end, the holding element 6 is moved relatively toward the carrier element 7. Particularly advantageously, provision is in this case made that an air cushion remains inside the sample vessel 1, so that the wash fluid 12 can be fully pressed out together with the foreign substances to be washed out.

In the first alternative, the reservoir 8 is arranged in a pan, so that the multiplicity of plungers 5 can engage into the reservoir 8 from above in order to be immersed in the wash fluid 12. The plungers 5 are in this case immersed in the same wash fluid 12 and therefore take the wash fluid 12 from the same reservoir 8.

Figure 4:
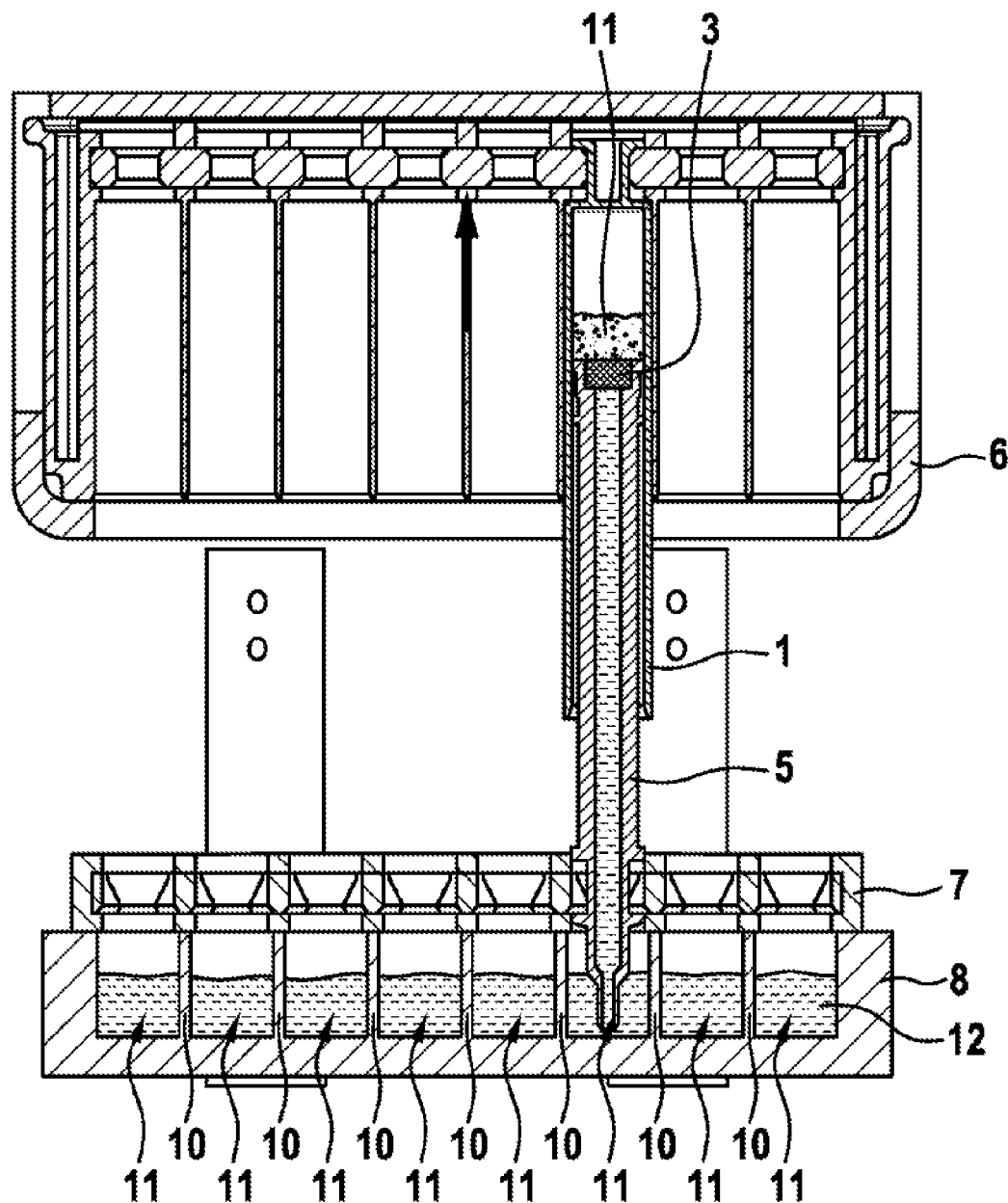
FIG. 4 shows a schematic view of a second alternative of a washing process of the method according to the exemplary embodiment of the invention.
Figure 5:
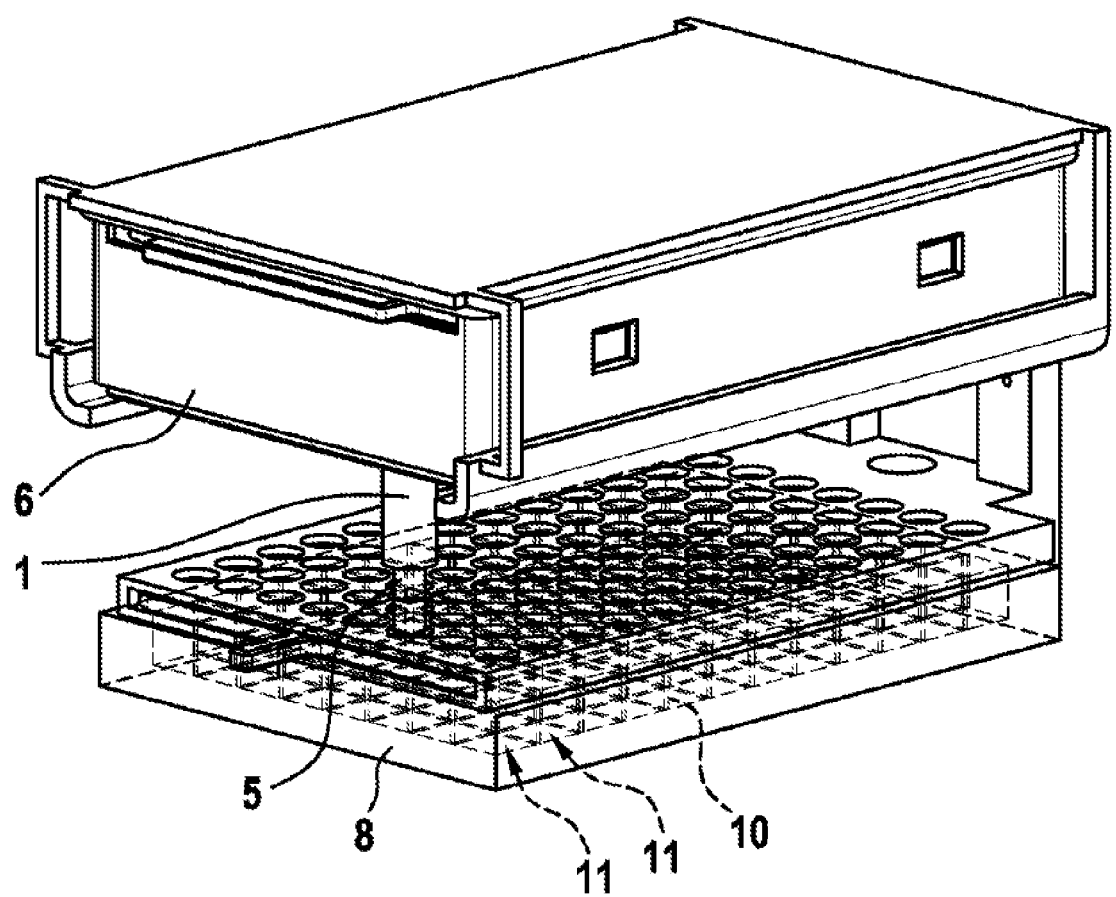
FIG. 5 shows a schematic view of the components used for carrying out the washing process according to the second alternative.

FIGS. 4 and 5 show a second alternative of the washing process 900. In this case, the second alternative corresponds essentially to the first alternative, with the only difference that the reservoir 8 is delimited into individual subreservoirs 11 by at least one, in particular retractable, subdivision element 10. In this way, in particular, the reservoir 8 is simply too early, in which only a single bowl of the wash fluid 12 is to be provided. Subsequently, the subdivision element 10 may be inserted. By the subdivision element, the reservoir 8 is divided into a multiplicity of subreservoirs 11, a separate subreservoir 11 being available for each plunger 5. As an alternative, it is likewise possible for each subreservoir 11 to be filled separately, so as to adjust a predetermined quantity of wash fluid 12 individually for each individual plunger 5.

Figure 6:
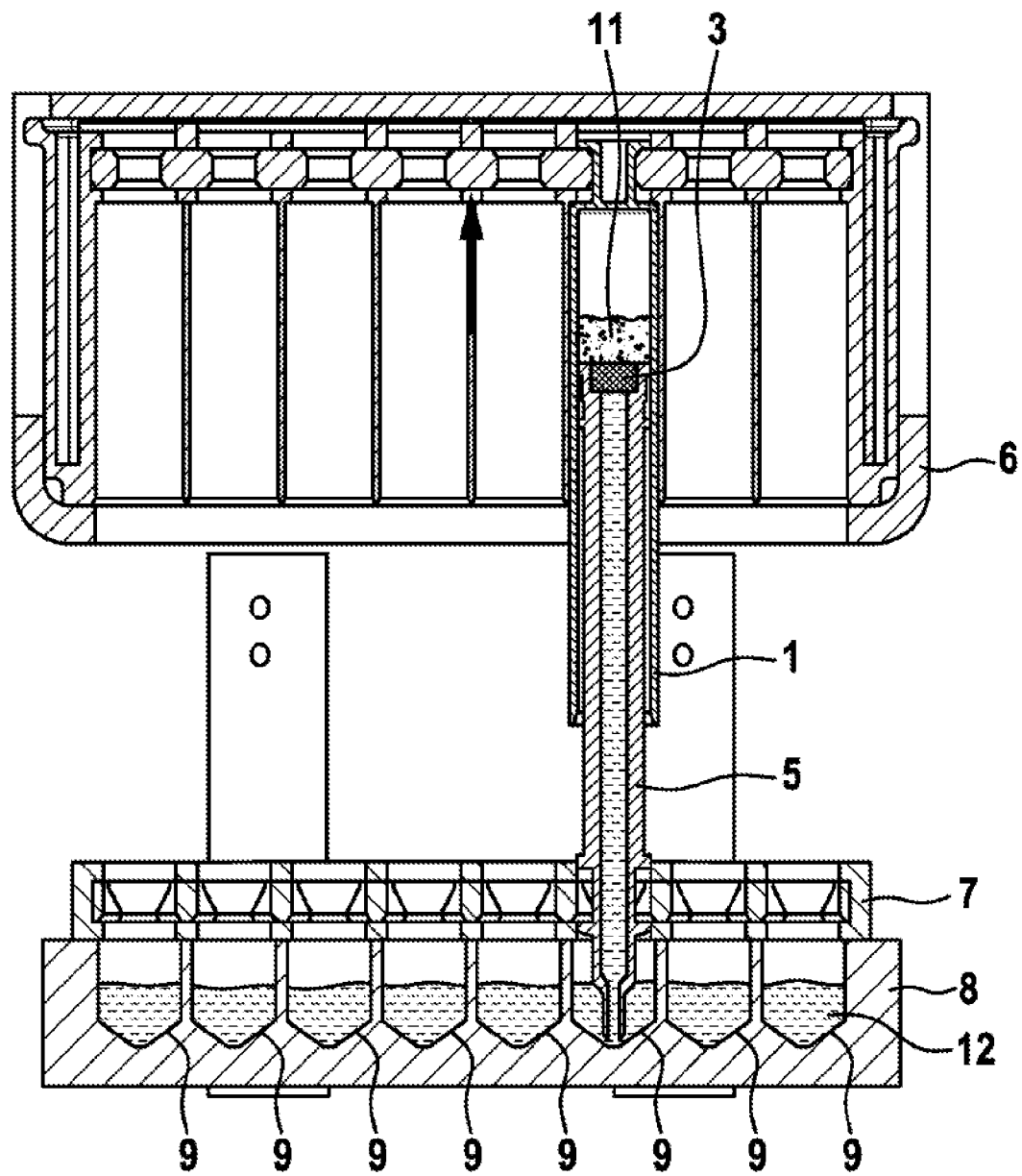
FIG. 6 shows a schematic view of a third alternative of a washing process of the method according to the exemplary embodiment of the invention.
Figure 7:
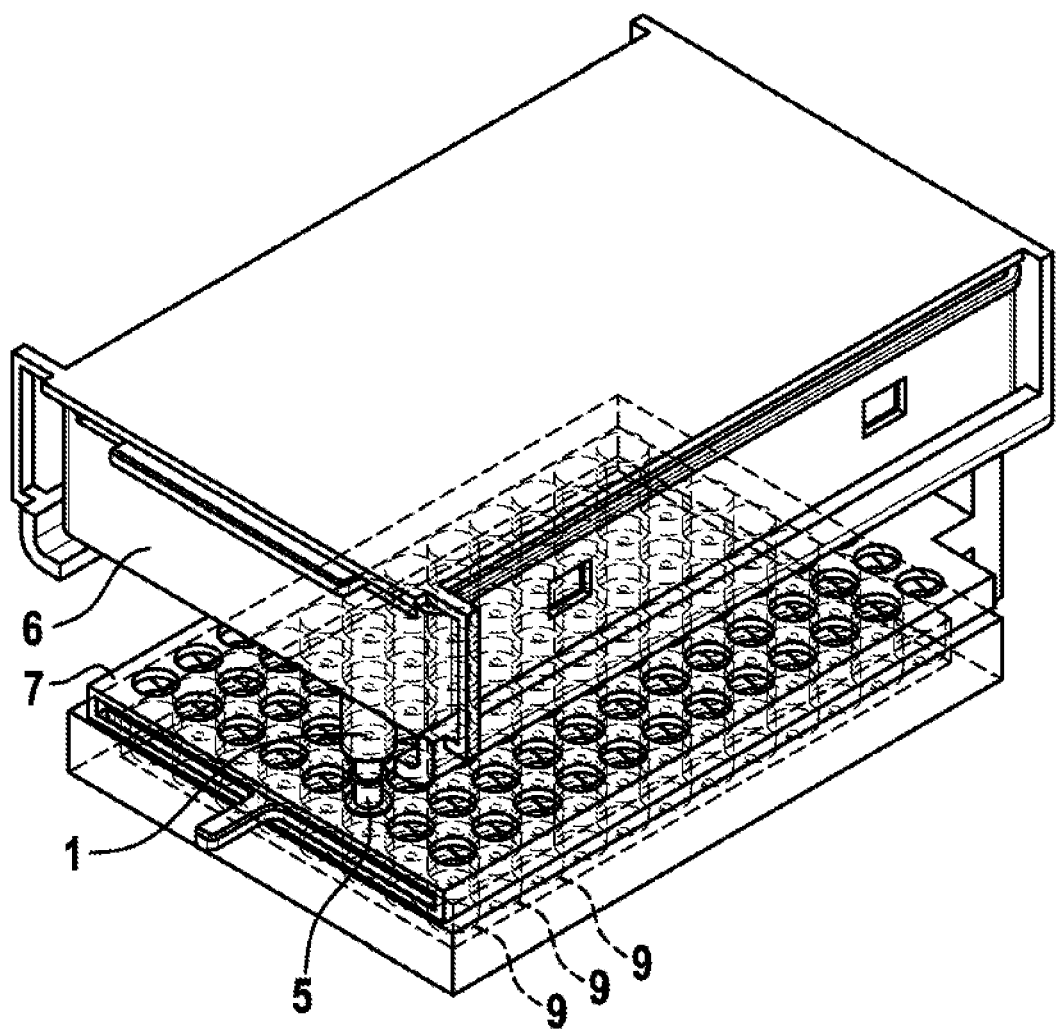
FIG. 7 shows a schematic view of the components used for carrying out the washing process according to the third alternative.

FIGS. 6 and 7 show a third alternative of the washing process 900. In contrast to the first alternative, a single reservoir 8 is not provided, rather there are a multiplicity of individual reservoirs 9 so that each plunger 5 is immersed in a separate individual reservoir 9. The amount of wash fluid 12 to be supplied to the respective sample vessel 1 can therefore be adjusted individually.

Figure 8:
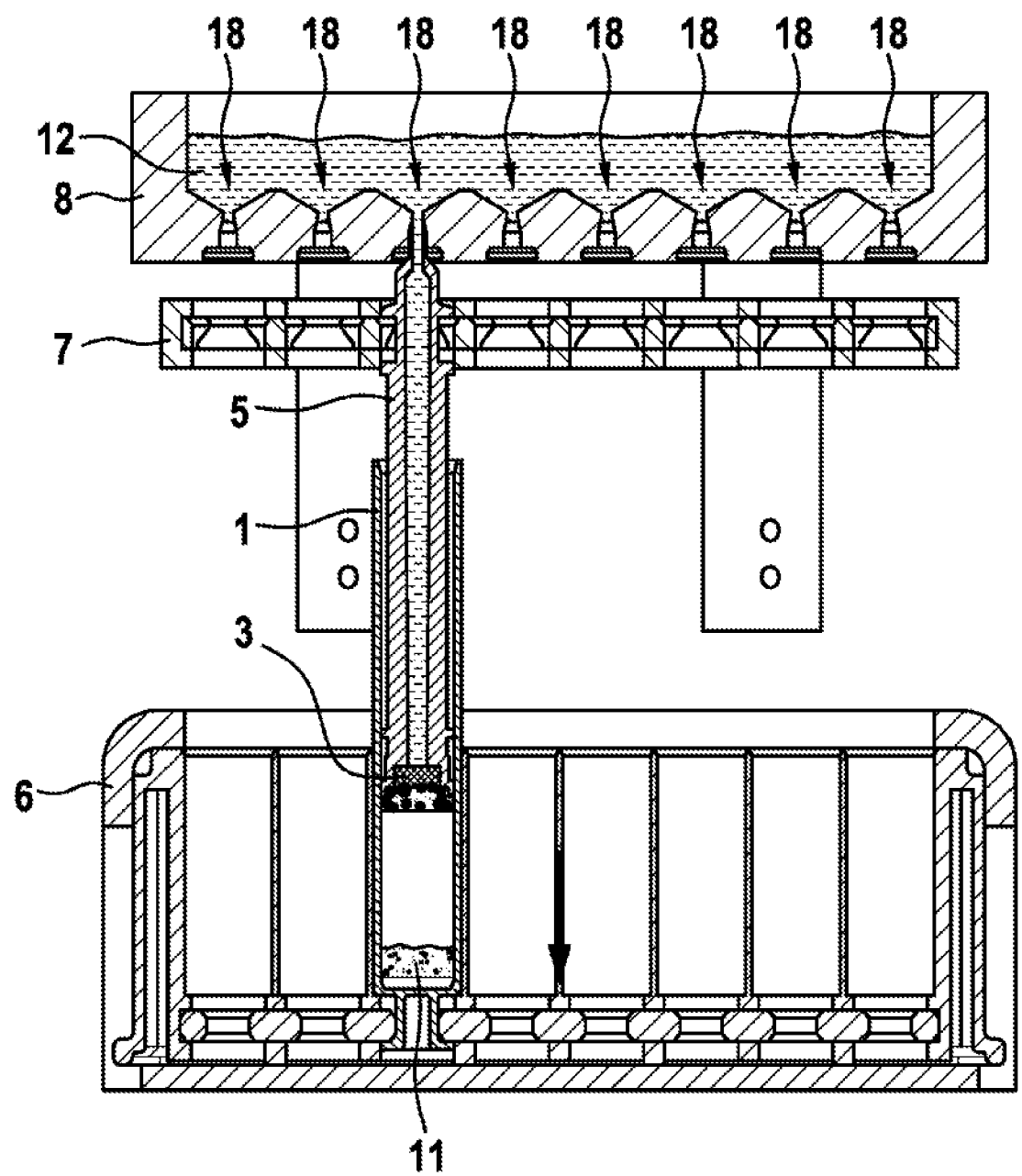
FIG. 8 shows a schematic view of a fourth alternative of a washing process of the method according to the exemplary embodiment of the invention.
Figure 9:
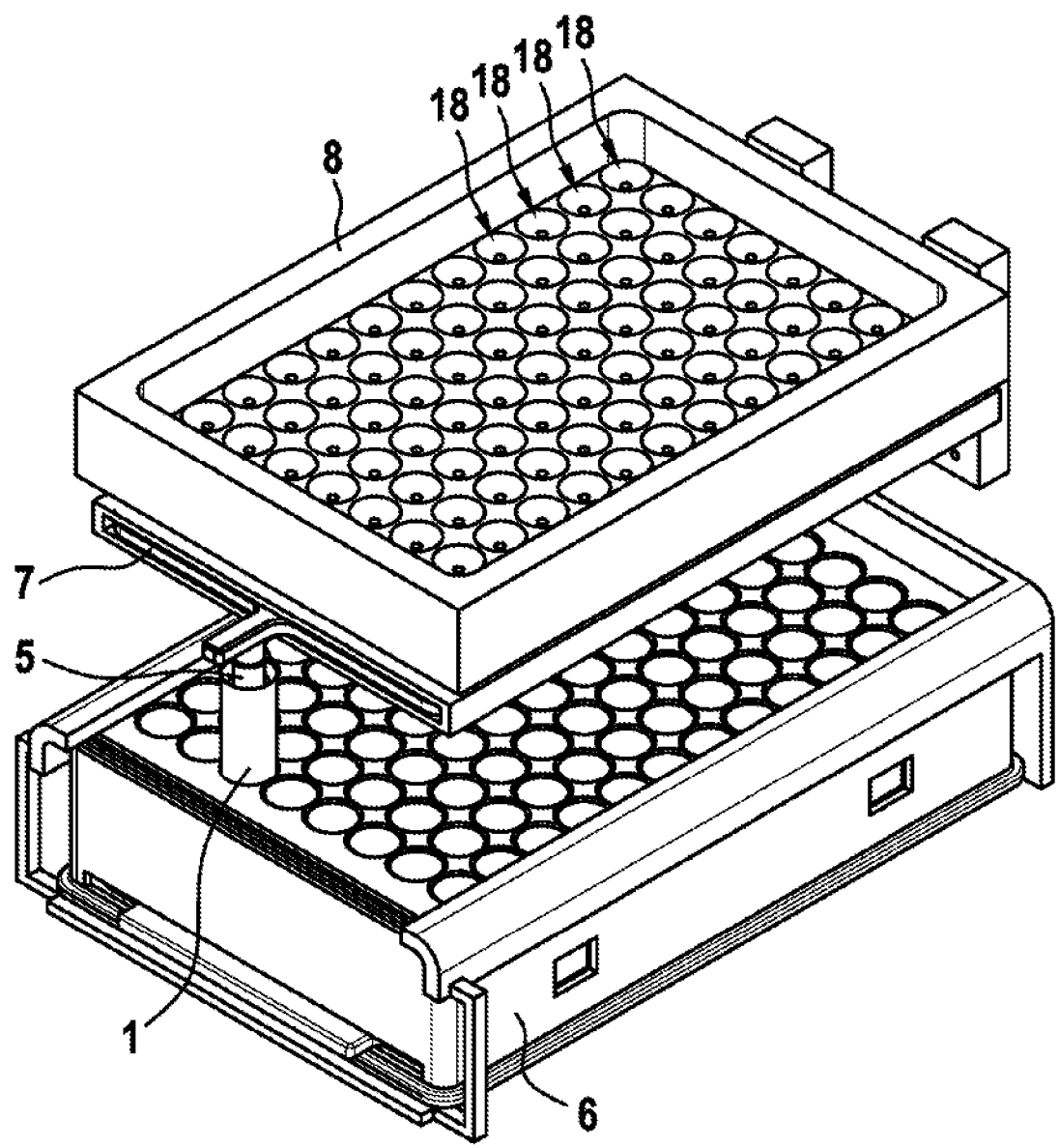
FIG. 9 shows a schematic view of the components used for carrying out the washing process according to the fourth alternative.

FIGS. 8 and 9 show a fourth alternative of the washing process 900. Again, provision is made for there to be a single reservoir 8, which is filled with the wash fluid 12. From this common reservoir 8, the wash fluid 12 is send in for each individual sample vessel, in which all the plungers 5 are immersed into the common reservoir 8. In contrast to the first alternative described above, however, immersion does not take place from above into the reservoir 8, but rather in a bottom of the reservoir 8 an opening 18 is provided, through which the multiplicity of plungers 5 can penetrate. Each plunger 5 is therefore assigned its own opening 18. The multiplicity of openings 18 are, in particular, fluid-tight so long as no plunger 5 penetrates through the opening 18. Filling of the reservoir 8 is advantageously carried out from above, so that a removal direction and a filling direction of the reservoir 8 are separate. Apart from the different removal direction, the removal of wash fluid 12 is carried out in a similar way to the first alternative.

Figure 10:
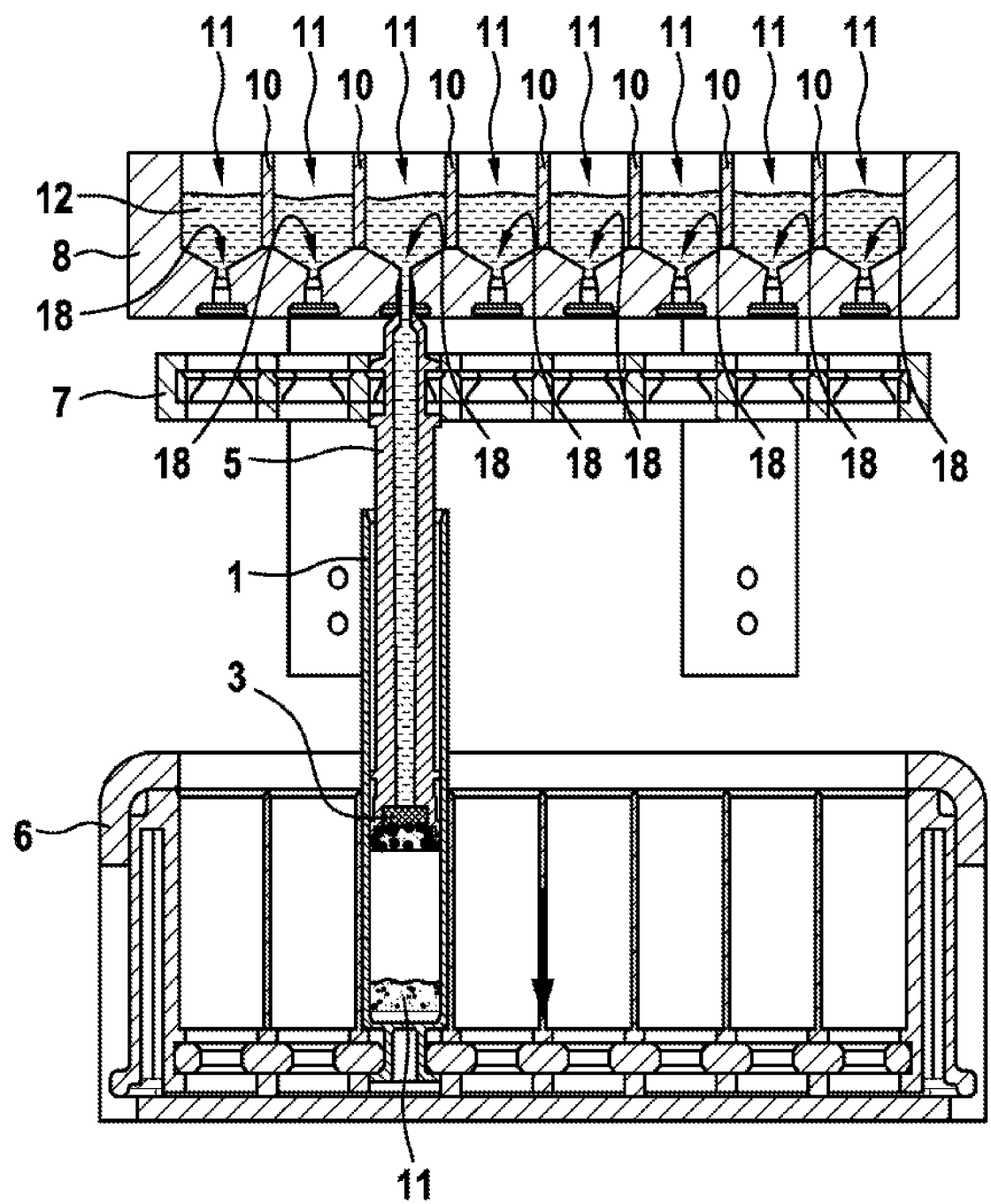
FIG. 10 shows a schematic view of a fifth alternative of a washing process of the method according to the exemplary embodiment of the invention.
Figure 11:
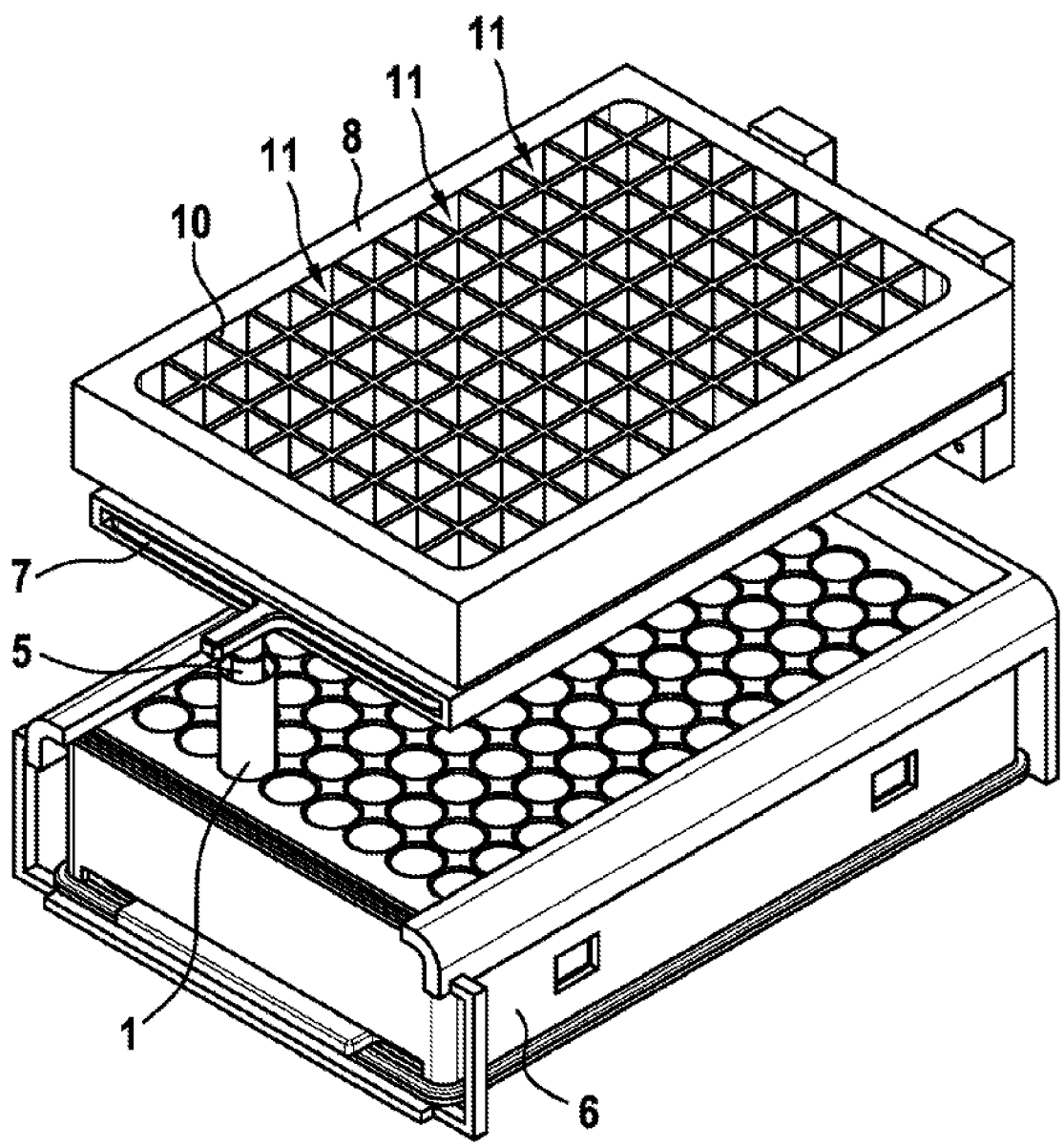
FIG. 11 shows a first schematic view of the components used for carrying out the washing process according to the fifth alternative.
Figure 12:
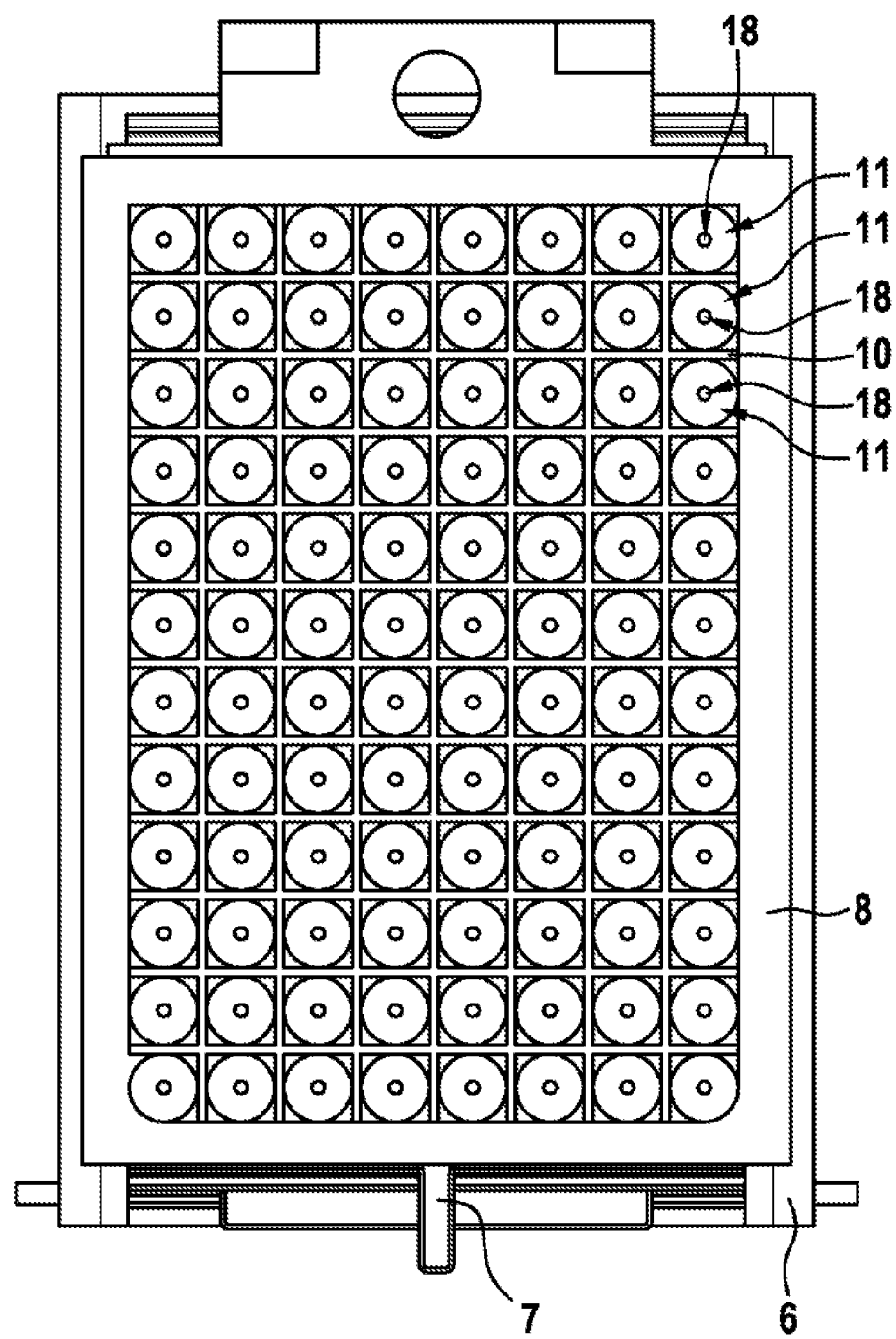
FIG. 12 shows a second schematic view of the components used for carrying out the washing process according to the fifth alternative.

FIGS. 10, 11 and 12 show a fifth alternative of the washing process 900. In this case, provision is again made that the common reservoir 8 is subdivided by at least one subdivision element 10 into a multiplicity of subreservoirs 11. Each of the subreservoirs 11 comprises an opening 18 described above. Removal of wash fluid 12 therefore again takes place from below through a bottom of the reservoir 8. In other regards, the washing process 900 according to the fifth alternative does not differ from the second alternative.

Figure 13:
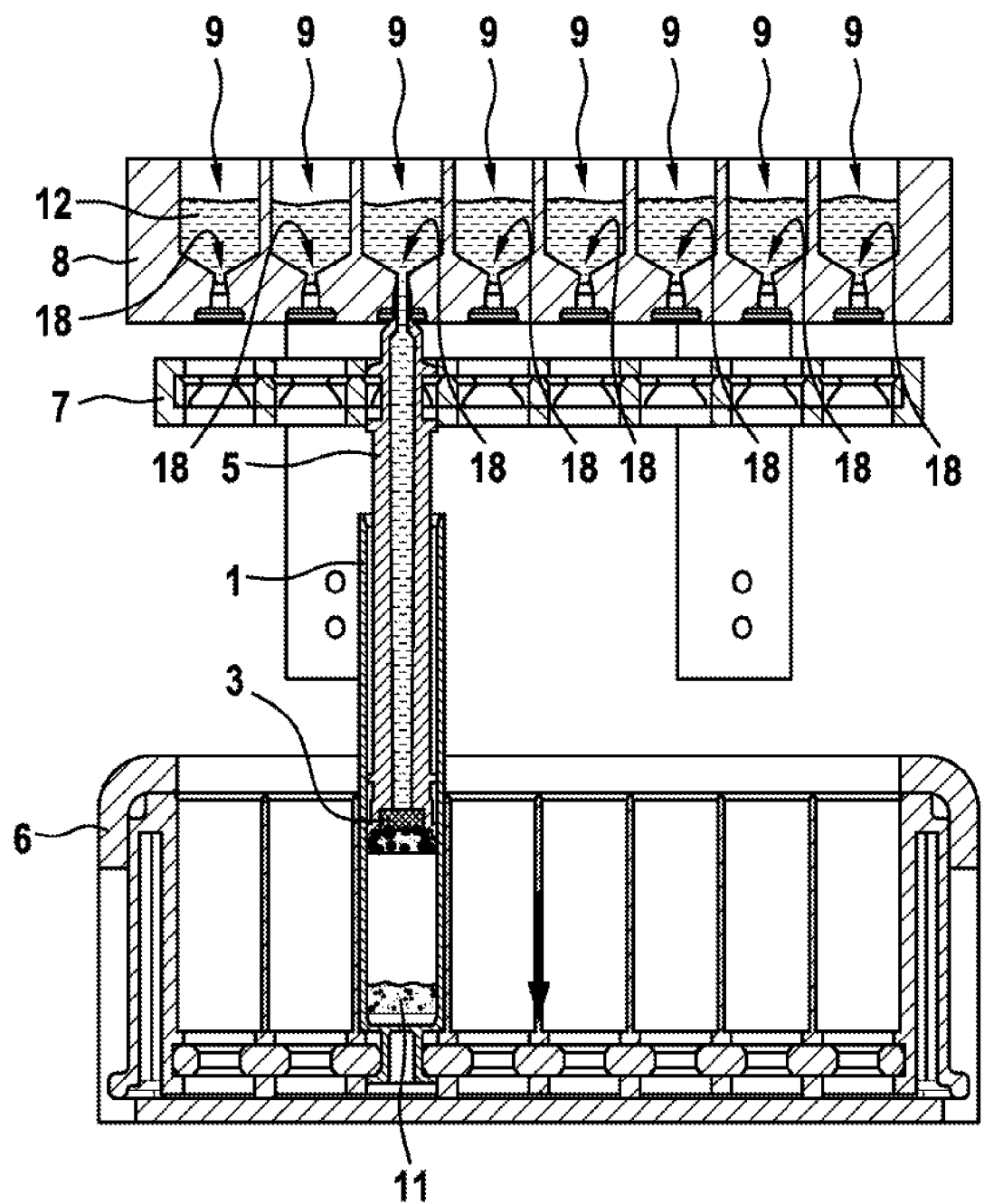
FIG. 13 shows a schematic view of a sixth alternative of a washing process of the method according to the exemplary embodiment of the invention.
Figure 14:
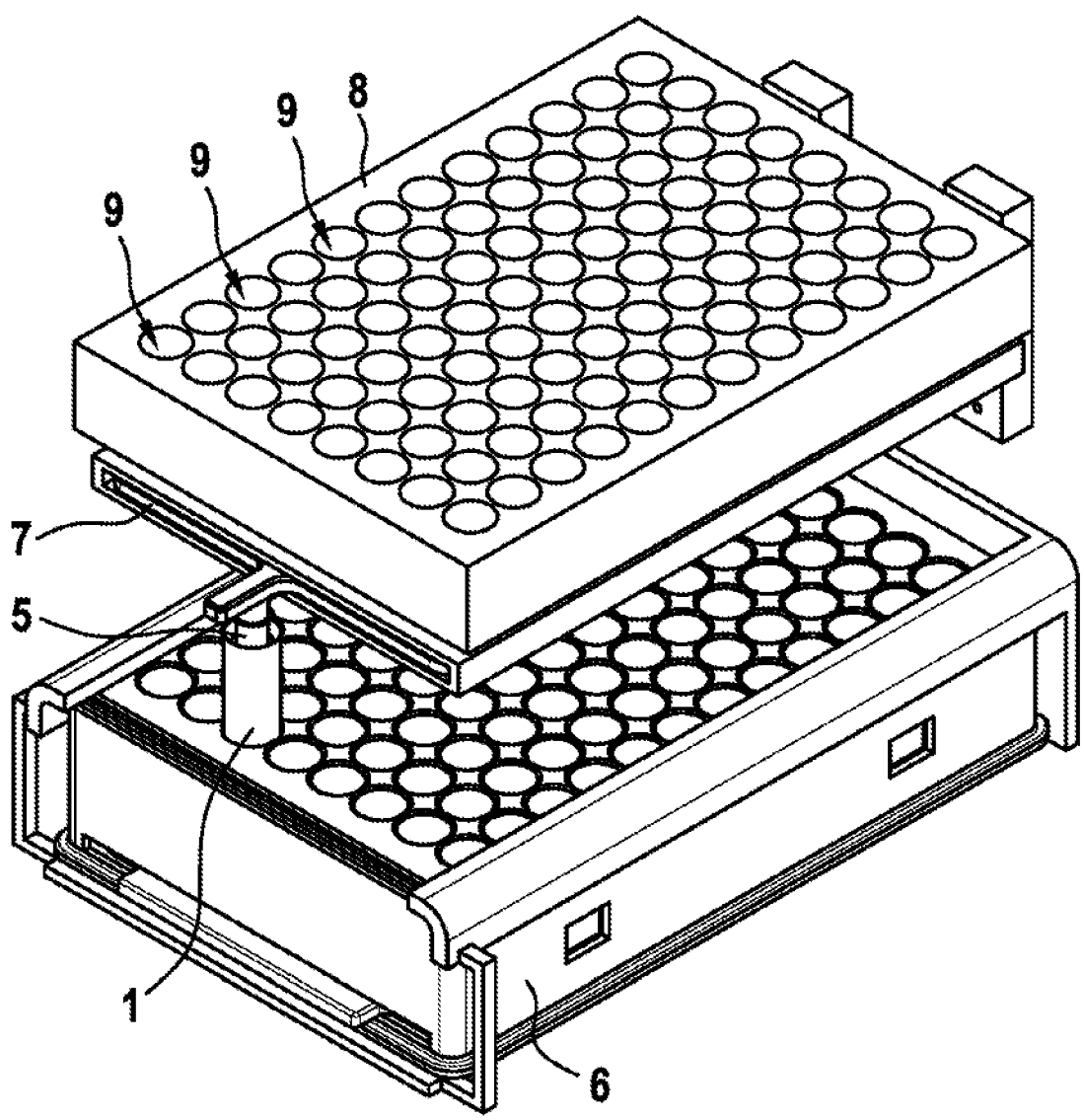
FIG. 14 shows a first schematic view of the components used for carrying out the washing process according to the sixth alternative.
Figure 15:
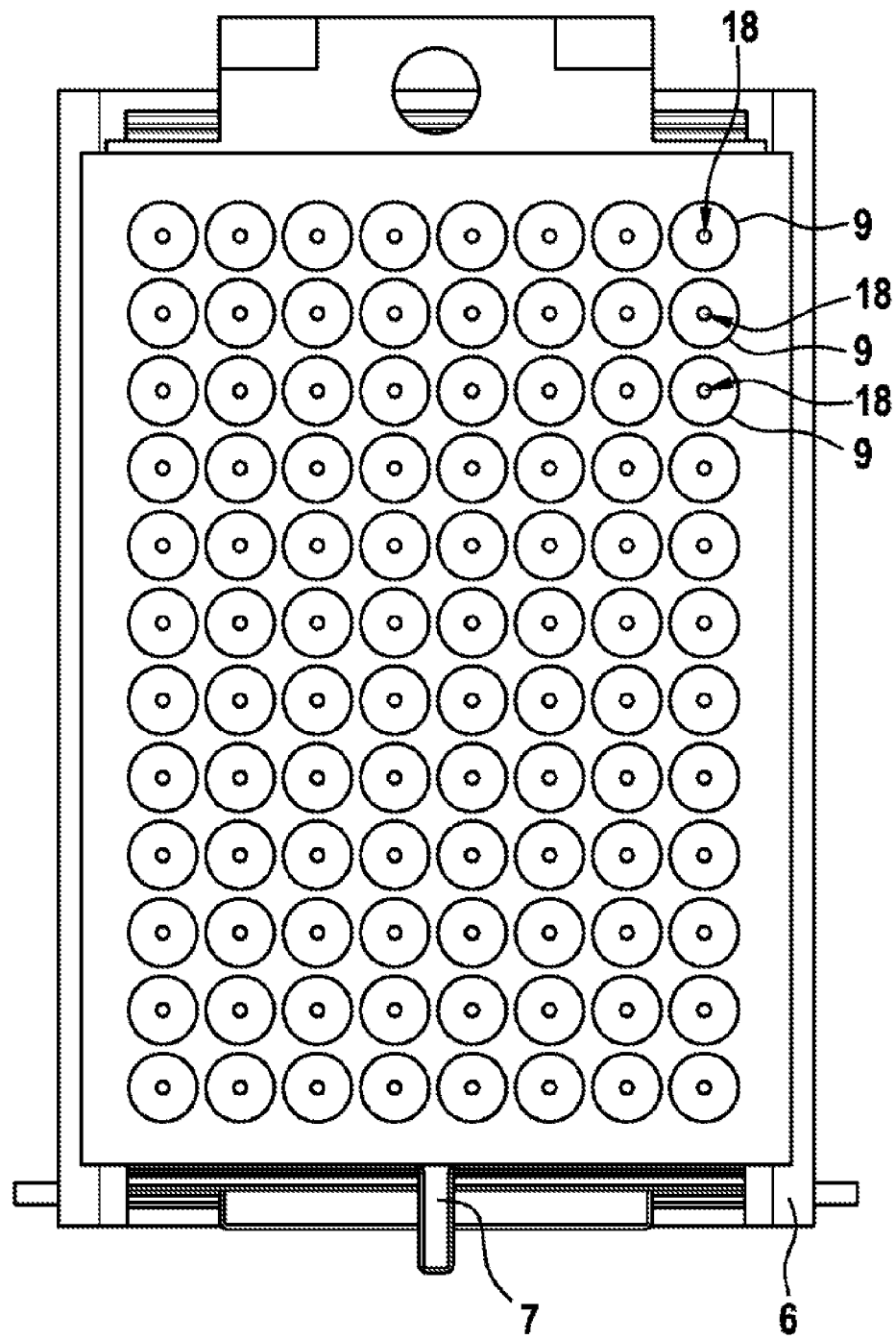
FIG. 15 shows a second schematic view of the components used for carrying out the washing process according to the sixth alternative.

FIGS. 13, 14 and 15 show a sixth alternative of the washing process 900. In this case, provision is again made for there to be a multiplicity of individual reservoirs 9, each individual reservoir 9 comprising an above-described opening 18. Each plunger 5 can therefore take wash fluid 12 out from the associated individual reservoir 9 through the corresponding opening 18. In contrast to the third alternative, removal of wash fluid 12 though the bottom of the multiplicity of individual reservoirs 9 is therefore again provided. In other regards, the washing process 900 according to the sixth alternative does not differ from the washing process 900 according to the third alternative.

If the wash fluid 12 is taken from above, as in the first alternative, the second alternative and the third alternative, precautions are to be taken against contamination of the wash fluid 12. At the same time, however, very accurate quantity assignment of wash fluid 12 to the respective samples vessel 1 is made possible. If, however, the wash fluid is taken from below, as in the fourth alternative, the fifth alternative and sixth alternative, the reservoir 8 or the individual reservoir 9 can be fully closed and therefore hermetically sealed from the environment. Wash fluid 12 can only be taken by the multiplicity of plungers penetrating through the openings 18. The reservoir 8 and/or the subdivision element 10 and/or the individual reservoirs 9 may preferably be used several times. A rinsing process and/or a cleaning process can, in particular, be carried out between the individual uses.

In all alternatives, provision is preferably made that the discharge 800 of the wash fluid 12 by pressing out the wash fluid 12 takes place into a separate waste container. In this way, the contamination risk is reduced.

The multiplicity of sample vessels 1 advantageously remain inside the holding element 6 during the entire washing process 900. To this end, the sample vessels 1 are capable of being fixed on the holding element 6. In particular, form-fit fixing is carried out, the form-fit fixing being releasable. In this way, the multiplicity of sample vessels 1, which are held by the holding element 6, can be handled simply and with little outlay. In particular, simultaneous conduct of a washing process 900 for a multiplicity of sample vessels 1 can be carried out. The effect therefore achieved is, in particular, that a throughput during the extraction of DNA is maximized. Particularly advantageously, each holding element 6 can receive a number of 96 sample vessels 1.

As for the washing process 900, provision is preferably made that the step of providing 400 the lysate 11 for a multiplicity of additional sample vessels 2 is also carried out simultaneously. The additional sample vessels 2 are held on an additional holding element (not shown) structurally equivalent to the holding element 6, the additional holding element also preferably being capable of receiving 96 additional sample vessels 2. In this way, in particular, the process of breaking down 200 the cellular material 13 is simplified, since a multiplicity of additional sample vessels 2 can be moved simultaneously by moving the additional holding element.

Figure 16:
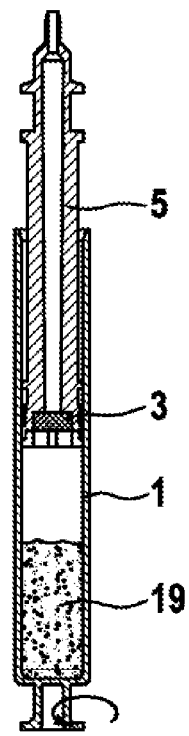
FIG. 16 shows a schematic view of a first mixing process during the method according to the exemplary embodiment of the invention.

In order to permit efficient mixing of the wash fluid 12 and the lysate 11 to form a purification mixture 19, provision is advantageously made that movement of the sample vessel 1 is carried out. This is represented in FIG. 16. The sample vessel 1 is, in particular, moved circularly at high frequency. In this way, optimal mixing takes place. Likewise, in this way particles adhering to the wash filter element 3 are released and mixed with the purification mixture 19. Such adhering particles are, in particular, DNA which has been retained by the wash filter element 3 because of the DNA-adsorbing substance 15. The mixing with the purification mixture 19 therefore ensures that the DNA is purified with a high quality.

Figure 17:
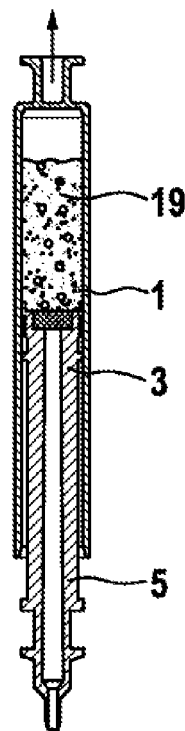
FIG. 17 shows a schematic view of a second mixing process during the method according to the exemplary embodiment of the invention.

FIG. 17 shows a further possibility of releasing particles from the wash filter element 3. To this end, after the delivery 800 of the wash fluid 12 by suction through the plunger 5, air is sucked in the same way through the plunger 5. This is therefore done by a relative movement between the plunger 5 and the sample vessel 1, particularly advantageously by the relative movement between the holding element 6 and the carrier element 7. By the loosening of particles from the wash filter element 3, the efficiency of the washing process 900 can be increased.

Figure 18:
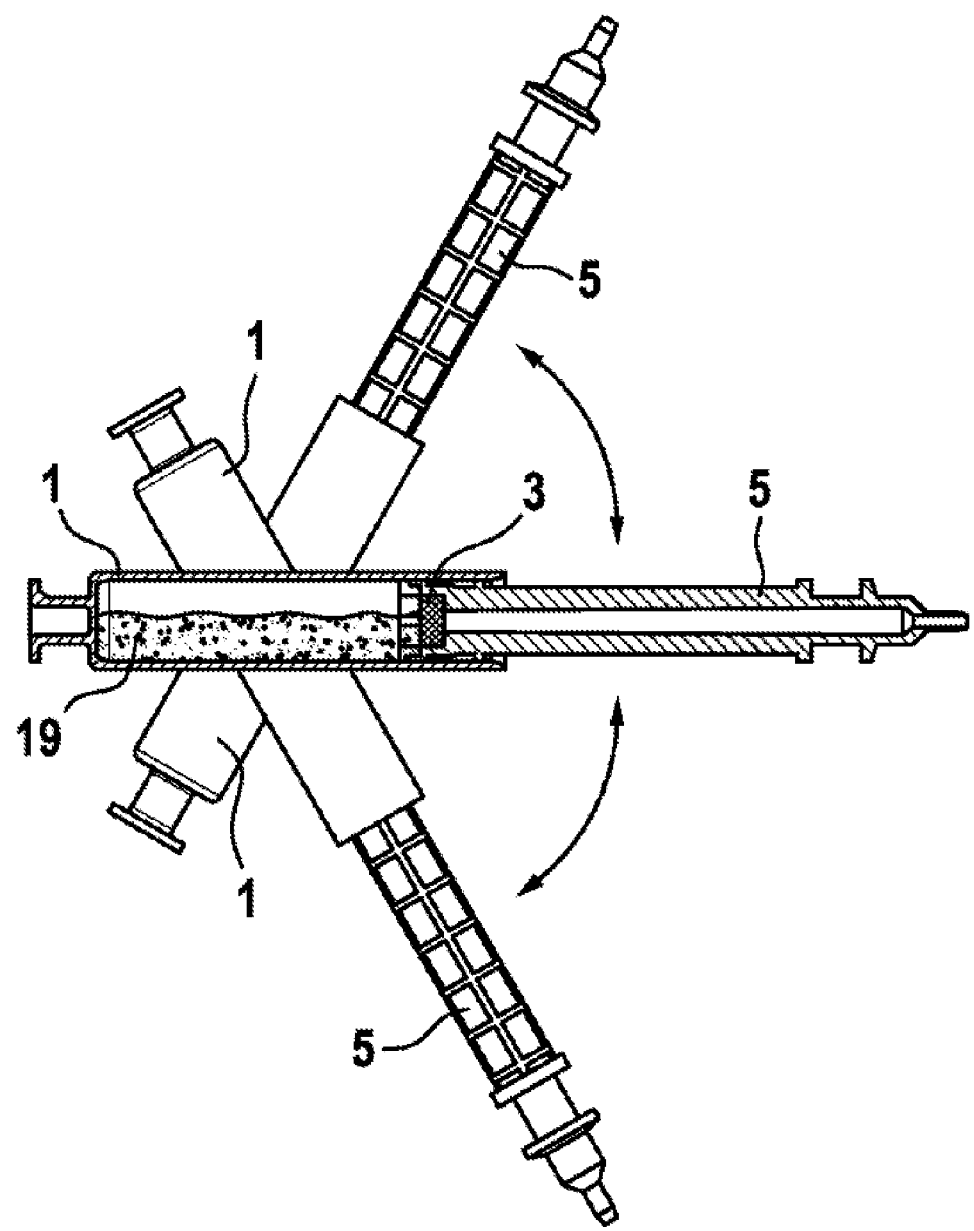
FIG. 18 shows a schematic view of a third mixing process during the method according to the exemplary embodiment of the invention.

Lastly, FIG. 18 shows a further possibility of releasing particles from the wash filter element 3 and ensuring optimal mixing of the purification mixture 19. To this end, alternating of the tilting of the sample vessel 1 and of the plunger 5 is carried out. Since the sample vessel 1 is closed in a fluid-tight fashion by the plunger 5, escape of fluid is in this case prevented.

Particularly advantageously, the DNA is present exclusively inside the sample vessel 1 during the entire washing process 900. Handling of the DNA is therefore possible in a very simple way and therefore optimally automatable. By the simple conduct of the washing process 900 by repeated relative movement of the holding element 6 and the carrier element 7, the washing process 900 can also be automated very simply and with little outlay. The same applies for the provision 400 of the lysate 4. Because of the simple automatability, a very large multiplicity of extractions of DNA can therefore be carried out simultaneously. In this case, the entire method takes place in sequential steps, and can therefore be controlled and monitored simply and with little outlay. At the same time, a high throughput is ensured because of the parallel conduct of the steps. Lastly, provision is advantageously made that highly pure DNA, which can be made available for further steps, can be extracted because of the described method according to the exemplary embodiment of the invention.

The invention claimed is:

1. A method for extracting DNA, comprising the steps:
lysing cells in a first sample vessel (2) to form a lysate,
filtering the lysate through a lysate filter element (4) into a second sample vessel (1) to form a filtered lysate (11) comprising DNA released from the cells,
adding a DNA-adsorbing substance (15) to the second sample vessel (1) comprising the DNA released from the cells, wherein the DNA-adsorbing substance binds to and forms a complex with at least some of the DNA released from the cells,
closing the second sample vessel (1) with a wash filter element (3) formed of the same material as the lysate filter element (4),
delivering a wash fluid (12) into the second sample vessel (1) through the wash filter element (3), and
discharging the wash fluid (12) from the second sample vessel (1) through the wash filter element (3), wherein the complex is retained within the second sample vessel (1) by the wash filter element (3), and wherein any DNA that is not bound to the DNA-adsorbing substance is not retained by the wash filter element (3),
introducing an additional substance into the second sample vessel (1) in order to separate the DNA-adsorbing substance (15) from the DNA, producing free DNA, and
separating the DNA-adsorbing substance from the free DNA in the second sample vessel (1), leaving the free DNA in the second sample vessel (1).

2. The method as claimed in claim 1, characterized in that the step of lysing cells to form a lysate comprises the following steps:
introducing cellular material (13) and a grinding element (14) into the first sample vessel (2), and
breaking down the cellular material (13) by moving the first sample vessel (2).

3. The method as claimed in claim 1, characterized in that the wash filter element (3) or the lysate filter element (4) is arranged in a plunger (5), the plunger (5) being insertable into the second sample vessel (1) or the first sample vessel (2), and, through the plunger (5),
the wash fluid (12) being sucked into the second sample vessel (1) and pressed out of the second sample vessel (1), or
the lysate (11) being pressed out from the first sample vessel (2) into the second sample vessel (1).

4. The method as claimed in claim 3, characterized in that the plunger (5) and the second sample vessel (1) or the first sample vessel (2) form a syringe.

5. The method as claimed in claim 1, characterized in that the second sample vessel (1) is held in a holding device (6) throughout the entire method, and/or the first sample vessel (2) is held in an additional holding device at least during the step of filtering the lysate (11).

6. The method as claimed in claim 5, characterized in that the holding element (6) simultaneously holds a multiplicity of second sample vessels (1), and/or the additional holding element simultaneously holds a multiplicity of first sample vessels (2), so that the method is applied simultaneously to the multiplicity of second sample vessels (1) and/or first sample vessels (2).

7. The method as claimed in claim 4, characterized in that a multiplicity of plungers (5) are fixed on a carrier element (7), so that, at the same time, the multiplicity of plungers (5) are inserted simultaneously into the multiplicity of second sample vessels (1) and/or first sample vessels (2).

8. The method as claimed in claim 7, characterized in that the step of delivering the wash fluid (12) and/or the step of discharging the wash fluid (12), and/or the step of filtering the lysate (11), are carried out by moving the carrier element (7) and the holding element (6) and/or the additional holding element relative to one another.

9. The method as claimed in claim 7, characterized in that the step of delivering the wash fluid (12) is carried out by simultaneous suction of wash fluid (12) through the multiplicity of plungers (5) from a common reservoir (8) or from an individual reservoir (9) provided for each plunger (5).

10. The method as claimed in claim 9, characterized in that the reservoir (8) is subdivided by at least one subdivision element (10) into individual subreservoirs (11) for each plunger (5).

11. The method as claimed in claim 1, characterized in that the steps of delivering the wash fluid (12) and of discharging the wash fluid (12) are carried out repeatedly.

12. The method as claimed in claim 1, characterized in that after the step of delivering the wash fluid (12) and before the step of discharging the wash fluid (12), air is delivered to the second sample vessel (1).

13. The method as claimed in claim 1, characterized in that after the step of delivering the wash fluid (12) and before the step of discharging the wash fluid (12), the second sample vessel (1) is moved circularly or alternatingly.

14. The method as claimed in claim 1, characterized in that the wash filter element (3) and the lysate filter element (4) are identical, and/or the second sample vessel (1) and the first sample vessel (2) are constructed identically.

15. The method as claimed in claim 1, characterized in that the step of lysing cells to form a lysate (11) comprises the following steps:
   introducing cellular material (13) and a grinding ball (14) into the first sample vessel (2), and
   breaking down the cellular material (13) by moving the first sample vessel (2) with frequency in an alternating movement.

16. The method as claimed in claim 9, characterized in that the reservoir (8) is subdivided by at least one retractable subdivision element (10) into individual subreservoirs (11) for each plunger (5).

17. The method as claimed in claim 1, characterized in that after the step of delivering the wash fluid (12) and before the step of discharging the wash fluid (12), air is delivered to the second sample vessel (1), the air being delivered to the second sample vessel (1) in the same way as the wash fluid (12).

18. The method as claimed in claim 1, characterized in that after the step of delivering the wash fluid (12) and before the step of discharging the wash fluid (12), the second sample vessel (1) is moved with a frequency, circularly or alternatingly.

19. The method as claimed in claim 1, characterized in that the additional substance is a chaotropic salt disrupts binding between the DNA and DNA-adsorbing substance to form a mixture of free DNA and the DNA-adsorbing substance.

20. The method as claimed in claim 19, characterized in that the DNA-adsorbing substance is coated on magnetic beads, and wherein a magnet is used to separate the DNA-adsorbing substance from the free DNA in the second sample vessel (1).

* * * * *